(12) United States Patent
Dubewar et al.

(10) Patent No.: US 12,097,197 B2
(45) Date of Patent: Sep. 24, 2024

(54) STABLE LIQUID COMPOSITIONS OF NETUPITANT AND PALONOSETRON

(71) Applicant: Slayback Pharma LLC, Princeton, NJ (US)

(72) Inventors: Ashish Anilrao Dubewar, Hyderabad (IN); Rahul Dhulaji Bhise, Hyderabad (IN); Mahadeo Vasant Mahadik, Hyderabad (IN); Shanker Mamidi, Nalgonda (IN); Mayur Anshiram Adhav, Hyderabad (IN); Raghavender Rao Kategher, Vikarabad (IN); Nagaraj Gangam, Hyderabad (IN); Sumitra Ashokkumar Pillai, Hyderabad (IN); Praveen Kumar Subbappa, Princeton, NJ (US)

(73) Assignee: Slayback Pharma LLC, Princeton (IN)

( * ) Notice: Subject to any disclaimer, the term of this patent is extended or adjusted under 35 U.S.C. 154(b) by 0 days.

(21) Appl. No.: 18/069,204

(22) Filed: Dec. 20, 2022

(65) Prior Publication Data
US 2023/0190737 A1 Jun. 22, 2023

(30) Foreign Application Priority Data
Dec. 21, 2021 (IN) .............................. 202141059731

(51) Int. Cl.
*A61K 31/497* (2006.01)
*A61K 9/00* (2006.01)
*A61K 31/473* (2006.01)

(52) U.S. Cl.
CPC .......... *A61K 31/497* (2013.01); *A61K 9/0019* (2013.01); *A61K 31/473* (2013.01)

(58) Field of Classification Search
CPC ... A61K 31/497; A61K 9/0019; A61K 31/473
See application file for complete search history.

(56) References Cited

U.S. PATENT DOCUMENTS

| | | |
|---|---|---|
| 6,297,375 B1 | 2/2001 | Bos |
| 8,426,450 B1 | 4/2013 | Fadini |
| 8,951,969 B2 | 2/2015 | Trento |
| 9,186,357 B2 | 11/2015 | Trento |
| 9,951,016 B2 | 4/2018 | Bacilieri |
| 10,624,911 B2 | 4/2020 | Venturini |
| 2020/0188368 A1* | 6/2020 | Chandrashekhar ....... A61P 1/08 |
| 2022/0273630 A1 | 9/2022 | Kocherlakota |

OTHER PUBLICATIONS

Manasa et al. ("International Journal of Advanced Research in Medical & Pharmaceutical Sciences" IJARMPS-ISSN-2455-6998) vol. 6, Issue.5, Sep.-Oct. 2021. (Year: 2021).*

* cited by examiner

*Primary Examiner* — Jean P Cornet
(74) *Attorney, Agent, or Firm* — Sarika Singh; McNeely, Hare & War LLP

(57) ABSTRACT

The present invention relates to stable liquid compositions suitable for parenteral administration in the form of a solution comprising:
(a) netupitant and optionally palonosetron;
(b) at least one pharmaceutically acceptable stabilizer;
(c) at least one pharmaceutically acceptable solubilizer; and
(d) at least one pharmaceutically acceptable vehicle,
wherein netupitant is present at a concentration of about 0.5 mg/mL to about 20 mg/mL and the solution has a pH of about 2 to about 6.

The compositions are suitable for subcutaneous, intravenous, or intramuscular administration. The invention further relates to methods for manufacturing the compositions and methods of using such compositions for prevention, treatment or management of nausea and vomiting.

24 Claims, No Drawings

STABLE LIQUID COMPOSITIONS OF NETUPITANT AND PALONOSETRON

FIELD OF THE INVENTION

The present invention relates to stable liquid pharmaceutical compositions comprising netupitant, alone or in combination with palonosetron, suitable for subcutaneous, intravenous, or intramuscular administration. The invention further relates to methods for manufacturing the compositions and methods of using such compositions for prevention, treatment or management of nausea and vomiting.

BACKGROUND OF THE INVENTION

Emesis is the act of vomiting and can be described as the forceful expulsion of gastrointestinal contents through the mouth brought about by the descent of the diaphragm and powerful contractions of the abdominal muscles. Emesis is usually, but not always, preceded by nausea. Nausea may be defined as a desire to vomit but which is not associated with expulsive muscular movement.

Vomiting and nausea can be caused by several factors including anaesthetics, radiation, cancer chemotherapeutic agents, toxic agents, medicines (for example serotonin reuptake inhibitors, analgesics such as morphine, antibiotics), pregnancy and surgery.

Two areas of clinical relevance are nausea and vomiting resulting from surgical procedures (post-operative nausea and vomiting, or PONV) or chemotherapeutic agents (chemotherapy-induced nausea and vomiting, or CINV) and radiation therapy (radiation therapy-induced nausea and vomiting, or RINV). Symptoms caused by chemotherapeutic agents such as nausea and vomiting can be so severe that the patient refuses further treatment. There are three types of emesis associated with the use of chemotherapeutic agents, i.e., acute emesis, delayed emesis, and anticipatory emesis. PONV is also a significant issue for patients and healthcare providers. It is rated second to pain as the most feared complication by patients and contributes significantly to anxiety and patient distress.

Several strategies have emerged in medical community to control nausea and vomiting caused by various medical procedures or treatment (such as chemotherapy, radiation therapy & surgery). With the development of the 5-HT$_3$ receptor antagonists in the early 1990s, there emerged new strategies in the medical community to better control nausea and vomiting caused by various medical procedures, including chemotherapy (CINV), surgery (PONV), and radiation therapy (RINV). When added to steroids such as dexamethasone, several 5-HT$_3$ antagonists have been demonstrated to significantly improve the standard of life for patients undergoing emetogenic medical procedures. Examples of 5-HT$_3$ antagonists include ondansetron, marketed by GlaxoSmithKline, and palonosetron, developed by Helsinn Healthcare.

Netupitant is a potent and selective NK-1 receptor antagonists which has been shown to be highly effective antiemetic in various pre-clinical and clinical models. The chemical name of netupitant is 2-[3,5-bis(trifluoromethyl) phenyl]-N, 2 dimethyl-N-[4-(2-methylphenyl)-6-(4-methylpiperazin-1-yl)pyridin-3-yl]propenamide and its chemical structure is represented by the structural Formula:

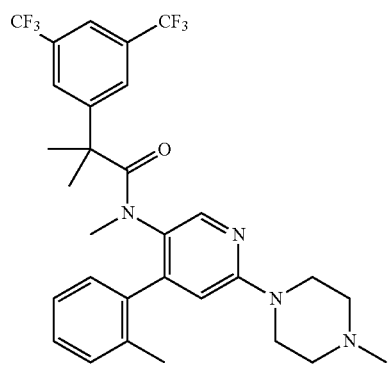 [SMILES: Cc1ccccc1-c1cc(N2CCN(C)CC2)ncc1N(C)C(=O)C(C)(C)c1cc(C(F)(F)F)cc(C(F)(F)F)c1]

Netupitant

Netupitant is white to off-white crystalline powder. Netupitant is characterized as a class II compound in the Biopharmaceutical Classification System (BCS), which means that it has low aqueous solubility and high permeability. Netupitant is very slightly soluble in water (less than 1 mg/mL). Hence, it is difficult to solubilize netupitant in water.

Palonosetron is a selective 5-hydroxytryptamine 3 (5-HT$_3$) antagonist used for the treatment of emesis. The chemical name of the hydrochloride salt of Palonosetron is (3aS)-2-[(S)-I-Azabicyclo[2.2.2]oct-3-yl]-2,3,3a,4,5,6-hexahydro-I-oxo-1Hbernz[de]isoquinoline hydrochloride, as depicted by the following chemical structure:

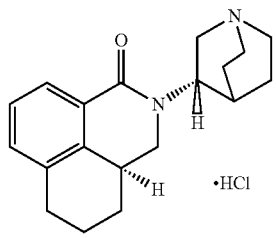 [SMILES: O=C1c2cccc3c2[C@H](CCC3)CN1[C@@H]1CN2CCC1CC2 ; Cl]

Palonosetron Hydrochloride

Palonosetron is white to off-white crystalline powder. Palonosetron hydrochloride is characterized as a class I compound in the Biopharmaceutical Classification System (BCS), which means that it has high aqueous solubility and high permeability.

Netupitant prevents nausea and vomiting during both acute and delayed phases of emesis, while palonosetron prevents nausea and vomiting during acute phase of emesis. It has been discovered that palonosetron is much more effective in combination with netupitant than with aprepitant, as reported by Grunberg et al., Support Cancer Care (2009) 17:589-594. In addition, palonosetron shows an improved pharmacokinetic profile (e.g., better bioavailability) when used in combination with netupitant. Netupitant also potentiates the effect of dexamethasone, such that the dexamethasone is effective even when administered at subtherapeutic doses (i.e., doses at which the dexamethasone would be ineffective if administered by itself).

Solid oral dosage forms have been developed that combine netupitant and palonosetron for the treatment of acute and delayed emesis. An oral product comprising netupitant and palonosetron has been approved by the Food and Drug Administration (FDA) and is marketed by Helsinn Healthcare in the form of hard gelatin capsules (300 mg netupitant;

EQ 0.5 mg base palonosetron) under the brand name AKYNZEO® (NDA 205718; National Drug Code Number 69639-101). AKYNZEO® is indicated in combination with dexamethasone for the prevention of acute and delayed nausea and vomiting associated with initial and repeat courses of cancer chemotherapy. Each AKYNZEO® capsule is composed of one white-caramel hard gelatin capsule which contains three tablets each containing 100 mg netupitant and one gelatin capsule containing 0.5 mg palonosetron (equivalent to 0.56 mg palonosetron hydrochloride). Label for AKYNZEO® at page 13. The inactive ingredients are butylated hydroxy anisole (BHA), croscarmellose sodium, gelatin, glycerin, magnesium stearate, microcrystalline cellulose, mono- and di-glycerides of capryl/capric acid, polyglyceryl dioleate, povidone K-30, purified water, red iron oxide, silicon dioxide, sodium stearyl fumarate, sorbitol, sucrose fatty acid esters, titanium dioxide and yellow iron oxide. Id.

The recommended dosage of AKYNZEO® capsules in adults for highly emetogenic chemotherapy (including cisplatin-based chemotherapy) is one capsule approximately 1 hour prior to the start of chemotherapy with 12 mg dexamethasone administered orally 30 minutes prior to chemotherapy on day 1, and 8 mg of dexamethasone on days 2 to 4. Label for AKYNZEO® at page 3. Further, in case of chemotherapy not considered highly emetogenic (including anthracyclines and cyclophosphamide-based chemotherapy), the administration of dexamethasone on days 2 to 4 is not recommended. Id.

It is known in the art that relatively high dose of a drug is required for oral dosage forms to achieve similar therapeutic efficacy when compared to injectable dosage forms. In addition, nausea and vomiting makes it difficult to administer oral dosage forms. Hence, there is a need for developing stable liquid formulations of netupitant alone or in combination with palonosetron, suitable for parenteral administration. However, stable liquid formulations containing netupitant are difficult to develop and challenging to manufacture because netupitant is highly insoluble in aqueous environment.

To overcome these challenges, a prodrug of netupitant, i.e., fosnetupitant, has been developed to improve the solubility of netupitant and obtain a viable stable liquid formulation suitable for parenteral administration. As fosnetupitant is rapidly converted to netupitant in vivo following IV administration, the pharmacology of fosnetupitant is mainly attributable to netupitant.

Injectable formulations comprising a combination of fosnetupitant and palonosetron are currently approved and marketed under the brand name AKYNZEO® in the form of lyophilized powder for injection as well as a ready-to-dilute solution for injection. Each vial of AKYNZEO® lyophilized powder for injection contains 235 mg fosnetupitant and 0.25 mg palonosetron (equivalent to 0.28 mg palonosetron hydrochloride) and the inactive ingredients are edetate disodium (6.4 mg), mannitol (760 mg), sodium hydroxide and/or hydrochloric acid (for pH adjustment). Label for AKYNZEO® at page 14. Each vial of AKYNZEO® ready-to-dilute solution for injection contains 235 mg fosnetupitant and 0.25 mg palonosetron and the inactive ingredients are edetate disodium (3.2 mg), mannitol (760 mg), water for injection, sodium hydroxide and/or hydrochloric acid (for pH adjustment). Id. Both lyophilized powder for injection & ready-to-dilute solution for injection are indicated in combination with dexamethasone in adults for the prevention of acute and delayed nausea and vomiting associated with initial and repeat courses of highly emetogenic cancer chemotherapy.

No stable liquid formulations of netupitant suitable for parenteral administration appear to be available, probably because of the poor solubility characteristics exhibited by netupitant in aqueous environment. There exists a need for liquid formulations of netupitant, alone or in combination with palonosetron, suitable for administration by intravenous or other parenteral routes, which are safe, therapeutically effective, and exhibit prolonged physical and chemical stability without any significant loss of potency.

SUMMARY OF THE INVENTION

In an aspect, the present invention relates to stable liquid compositions suitable for parenteral administration comprising:
  (a) netupitant;
  (b) at least one pharmaceutically acceptable stabilizer;
  (c) at least one pharmaceutically acceptable solubilizer; and
  (d) at least one pharmaceutically acceptable vehicle,
    wherein netupitant is present at a concentration of about 0.5 mg/mL to about 20 mg/mL, and
    wherein the composition is in the form of a solution and has a pH of about 2 to about 6.

In some embodiments, the liquid compositions further comprise palonosetron.

In other embodiments, the compositions further comprise one or more pharmaceutically acceptable excipients selected from the group consisting of nucleation inhibiting agents, tonicity contributing agents, surfactants, buffers, pH adjusting agents, chelating agents, anti-oxidants, anti-foaming agents and preservatives.

In some embodiments, the solubilizer is selected from cyclodextrin, cyclodextrin derivatives, polysorbates, propylene glycol, polyethylene glycol or mixtures thereof.

In some embodiments, the stabilizer is selected from tromethamine, phosphoric acid, aspartic acid, tartaric acid, citric acid or mixtures thereof.

In some embodiments, the anti-oxidant is selected from sodium ascorbate, ascorbic acid, butylated hydroxytoluene, monothioglycerol, sodium thiosulfate, sodium formaldehyde sulfoxylate or mixtures thereof.

In some embodiments, the vehicle is selected from ethanol, water for injection or mixtures thereof.

In another aspect, the stable liquid compositions of the invention are injectable solutions suitable for subcutaneous, intravenous, or intramuscular administration. In certain aspects, the inventive compositions are suitable for intravenous bolus or intravenous infusion administration.

The solution of the invention may be an aqueous or non-aqueous solution.

In another aspect, the stable solutions of the invention are provided as a unit dosage form in a sealed container selected from ampoules, vials, and pre-filled syringes.

In another aspect, the stable solutions are advantageously ready-to-use (RTU) or ready-to-dilute (RTD).

In some embodiments, the stable solution comprises palonosetron at a concentration ranging from 0.001 mg/mL to about 0.1 mg/mL.

In some embodiments, the pH of the solution of the invention ranges from about 2.5 to about 6.

In some embodiments, the solution of the invention is stable for at least 2 months upon storage at a temperature of 2-8° C. In some embodiments, the solution of the invention is stable for at least 2 months upon storage at a temperature of 25° C. at 60% relative humidity (25° C./60% RH). In some embodiments, the solution of the invention is stable for at least 2 months upon storage at a temperature of 40° C. and 75% relative humidity (40° C./75% RH).

In an aspect, the stable solution of the invention has a level of each known impurity in the solution of less than about 0.5% w/w, as measured by HPLC.

In some embodiments, the stable solution of the invention comprises a) netupitant; b) ethanol; c) propylene glycol; d) polysorbate 80; e) water, and f) one or more pharmaceutically acceptable stabilizers.

In another embodiment, the stable solution of the invention comprises a) netupitant; b) ethanol; c) HPβCD; d) polysorbate 80; e) one or more pharmaceutically acceptable stabilizers, f) one or more pharmaceutically acceptable antioxidants and g) water.

In another embodiment, the stable solution of the invention comprises a) netupitant; b) palonosetron hydrochloride; c) HPβCD; d) polysorbate 80; e) one or more pharmaceutically acceptable stabilizers, f) one or more pharmaceutically acceptable antioxidants g) ethanol and h) water.

In another aspect, the present invention provides a stable solution suitable for parenteral administration comprising:
(a) netupitant;
(b) palonosetron hydrochloride;
(c) a pharmaceutically acceptable stabilizer;
(d) a pharmaceutically acceptable solubilizer; and
(e) a pharmaceutically acceptable vehicle, wherein the solution exhibits bioequivalence to reference drug product-1 or reference drug product-2 (as defined herein) upon administration to a subject in need thereof.

In another aspect, the present invention provides a unit dosage form comprising the stable solution of the invention suitable for parenteral administration comprising (a) 197.5 mg of netupitant, and (b) 0.28 mg of palonosetron hydrochloride.

In another aspect, the present invention provides a method for prevention of acute and/or delayed nausea and/or vomiting associated with initial and/or repeat courses of cancer chemotherapy in a subject in need thereof comprising parenteral administration of a stable solution of the invention comprising (a) a therapeutically effective amount of netupitant, and (b) a therapeutically effective amount of palonosetron hydrochloride.

DETAILED DESCRIPTION OF THE INVENTION

Unless defined otherwise, all the technical and scientific terms used herein have the same meanings as commonly known to a person of ordinary skill in the art. In case there is a plurality of definitions for the terms used herein, the definitions provided herein will prevail.

As used herein, "a," "an," "the," "at least one," and "one or more" are used interchangeably. As used herein, the term "or" is generally employed in its usual sense including "and/or" unless the content clearly dictates otherwise.

As used herein the term "netupitant" refers to netupitant free base or a pharmaceutically acceptable salt, solvate or hydrate thereof. It also includes geometric isomer or a stereoisomer thereof. Any crystalline as well as the amorphous form of netupitant may be used for the preparation of compositions of the present invention.

As used herein, the term "palonosetron" refers to palonosetron free base or a pharmaceutically acceptable salt, solvate, prodrug or hydrate thereof. It also includes geometric isomer or a stereoisomer thereof. In some embodiments, palonosetron hydrochloride may be used. Any crystalline as well as the amorphous form of palonosetron may be used for the preparation of compositions of the present invention.

The terms "about" and "approximate", when used along with a numerical variable, generally means the value of the variable and all the values of the variable within an experimental error (e.g., 95% confidence interval for the mean) or within a specified value±10% or within a broader range.

Within the context of the present invention, the term "ready-to-use" or "RTU" as used herein refers to an injectable composition that is stable and is not reconstituted from a lyophilizate. The term "ready-to-use" or "RTU" also encompasses within its scope, injectable compositions that does not require any reconstitution or dilution with parenterally acceptable diluent and can be directly administered to the patient.

Within the context of the present invention, the term "ready-to-dilute" or "RTD" as used herein refers to an injectable composition that is diluted with a suitable diluent for parenteral administration.

Within the context of the present invention, the term "reference drug product-1" as used herein refers to a ready-to-dilute injectable product comprising fosnetupitant and palonosetron, approved by the U.S. Food and Drug Administration (USFDA) under New Drug Application (NDA) number 210493 and National Drug Code (NDC) number 69639-105.

Within the context of the present invention, the term "reference drug product-2" as used herein refers to a lyophilized injectable product comprising fosnetupitant and palonosetron, approved by the U.S. Food and Drug Administration (USFDA) under New Drug Application (NDA) number 210493 and National Drug Code (NDC) number 69639-102.

The term "pharmaceutically acceptable liquid vehicle," "pharmaceutically acceptable vehicle," "parenterally acceptable liquid vehicle" and "vehicle" are used interchangeably.

The term "parenteral" or "injectable" refers to routes selected from subcutaneous (SC), intravenous (IV), intramuscular (IM), intradermal (ID), intraperitoneal (IP) and the like.

"Bioequivalence" refers to the absence of a significant difference between the bioavailability, i.e., the mean ratio of AUC ((the area under the curve) over 24 hours) and the mean ratio of $C_{max}$ (maximum (or peak) serum concentration) in blood plasma is within 80% to 125% between two pharmaceutical drug products (e.g., a test composition and a reference composition) over the course of a period, at the same dose and under the same conditions. The determination of whether a test composition is bioequivalent to a reference composition is determined by performing a study, referred to as a bioequivalence or comparative bioavailability study, in a group of subjects under controlled conditions.

The term "subject" refers to an animal, including a human or non-human. The terms patient and subject may be used interchangeably herein. Non-human animal may be a rat, a cat, a dog, a pig, a rabbit, a mouse, or a guinea pig.

The term "$C_{max}$" as used herein, refers to a maximum concentration of a drug in blood, serum, a specified compartment, or test area of a subject between administration of a first dose and administration of a second dose. The term $C_{max}$ could also refer to dose normalized ratios if specified. As used herein, "$C_{12h}$" refers to the plasma concentration measured at 12 hours from administration.

The term "$T_{max}$," as used herein, refers to a time or period after administration of a drug when the maximum concentration ($C_{max}$) is reached in blood, serum, a specified compartment, or test area of a subject. As used herein, "$T_{1/2}$" refers to the time at which the plasma concentration is half of the observed maximum.

The term "$AUC_{0-\infty}$", means the area under a plasma drug concentration—time curve from time point of 0 to infinity after drug administration.

The term "$AUC_{0-t}$," means the area under a plasma drug concentration—time curve from time points of 0 to t after drug administration, wherein t is time in hours and is in between 1 hour to 72 hours.

As used herein, the term "storage" refers to the holding of a composition under controlled or uncontrolled conditions for a period ranging from a few minutes to several months or longer. Storage conditions that can be controlled include, for example, temperature, humidity, and the level of light. In many cases, storage of a pharmaceutical formulation is under industry acceptable standards and/or standards that are mandated by regulatory agencies, such as USFDA.

The objective of the present invention is to increase the solubility of netupitant enabling formulation of netupitant solution product. Another objective of the present invention is to provide stable aqueous solutions of netupitant and palonosetron having long-term storage stability.

The inventive pharmaceutical compositions described herein may be provided in the form of a solution suitable for injection. To prepare such composition, active drug is dissolved in a parenterally acceptable liquid vehicle.

The pharmaceutically acceptable liquid vehicles may be any combination of pharmaceutically acceptable liquids suitable for parenteral administration. Suitable vehicles include ethanol, liquid polyethylene glycol, and propylene glycol, water, water for injection, isotonic sodium chloride solution, fixed oils, such as corn oil, cottonseed oil, peanut oil, and sesame oil, and suitable mixtures thereof.

As used herein, when pH of the composition is referred to in the context of a non-aqueous vehicle for the liquid compositions of the invention, the pH value refers to the measurement obtained when a simple extraction procedure using water is used for measuring the pH of the non-aqueous solution. Water is added and mixed thoroughly with the sample. After reaching equilibrium, the solvent phase is separated, if immiscible, and the pH of the water phase is then measured.

In some embodiments, the vehicle is selected from the group consisting of ethanol, water, water for injection, isotonic sodium chloride solution, or suitable mixtures thereof.

In an embodiment of the invention, the ready-to-use or ready-to-dilute compositions may be formulated as aqueous or non-aqueous solutions. Preferably, the ready-to-use or ready-to-dilute compositions will include a vehicle in an amount from about 5 mL to greater than or equal to 250 mL.

According to the present invention, the ready-to-dilute compositions may be provided in a kit form along with parenterally acceptable diluent. Parenterally acceptable diluents include water for injection, 0.9% saline (normal saline), 0.45% saline (half normal saline), 2.5% dextrose/ 0.45% saline, 5% dextrose solution, ringer's solution, and ringer's lactate solution.

In certain non-limiting embodiments, netupitant is formulated as a composition, wherein netupitant is the only therapeutically active ingredient present in the composition. In another non-limiting embodiment, netupitant is combined with palonosetron and formulated as a composition. In yet another non-limiting embodiment, netupitant is combined with palonosetron and dexamethasone and formulated as a composition.

In some embodiments, netupitant is present at a concentration of about 0.5 mg/mL or more. In some embodiments, stable ready-to-use or ready-to-dilute solutions of the present invention comprise netupitant, wherein netupitant is present at a concentration about 0.5 mg/mL, about 0.987 mg/mL, about 1.975 mg/mL, about 3.95 mg/mL, about 13.13 mg/mL, or about 15.2 mg/mL.

The stable ready-to-use or ready-to-dilute solutions of the present invention may comprise netupitant at a concentration ranging from about 0.5 mg/mL to about 30 mg/mL, or from about 0.5 mg/mL to about 25 mg/mL. In some embodiments, stable ready-to-use solutions of the present invention comprise netupitant at a concentration ranging from about 0.5 mg/mL to about 5 mg/mL. In some embodiments, stable ready-to-dilute solutions of the present invention comprise netupitant at a concentration ranging from about 10 mg/mL to about 17 mg/mL.

The present invention further relates to injectable solutions of netupitant and palonosetron, wherein palonosetron is present at a concentration of about 0.001 mg/mL or more. For example, palonosetron hydrochloride is may be present at a concentration of about 0.0014 mg/mL, about 0.0028 mg/mL, about 0.0056 mg/mL, about 0.0186 mg/mL, or about 0.0215 mg/mL.

In certain embodiments of the present invention, solubility of netupitant is increased by one or more of the methods selected from a) particle size reduction, b) solid dispersion, c) complexation, d) high-speed stirring, e) in situ salt formation, and/or f) use of solubilizing agents.

The solubilizer is any suitable compound that increases the solubility of netupitant in the chosen pharmaceutical acceptable vehicle. In some embodiments, the liquid composition comprises at least one solubilizer selected from cyclodextrin, cyclodextrin derivatives, polysorbates, propylene glycol, and polyethylene glycol or mixtures thereof. The amount of solubilizer may range from about 0.1 mg/mL to about 200 mg/mL of the composition, and preferably from about 0.5 mg/mL to about 100 mg/mL.

Cyclodextrins used in the present invention include α-cyclodextrin, substituted or non-substituted β-cyclodextrin, δ-cyclodextrin, γ-cyclodextrin, or combinations thereof. Examples of substituted β-cyclodextrins include those substituted with one or more hydrophilic groups, such as monosaccharide (e.g., glucosyl, maltosyl), carboxyalkyl (e.g., carboxyl methyl, carboxyethyl), hydroxyalkyl-substituted (e.g., hydroxyethyl, 2-hydroxypropyl) and sulfoalkylether-substituted-β-cyclodextrin.

In some embodiments, the cyclodextrin is a substituted β-cyclodextrin, particularly, hydroxypropyl-β-cyclodextrin (HP-β-CD) and sulfobutylether-β-cyclodextrin (SBE-β-CD). However, it is understood that typically any substitution to the cyclodextrin, including substitution by hydrophobic groups such as hydroxyalkyl-substituted-cyclodextrin, will improve its aqueous solubility by disrupting the hydrogen-bonding network within the crystal lattice of the solid cyclodextrin, thereby lowering the lattice energy of the solid. The degree of substitution is not believed to be critical; however, the degree of substitution is advantageously at least 1% and typically 2% to 10%, such as 3% to 6%.

Particularly suitable β-cyclodextrins include for example but not limited to, Cavasol® W7 HP (hydroxypropyl-β-cyclodextrin (HP-β-CD), Kleptose® HP (hydroxypropyl-β-cyclodextrin (HP-β-CD)), Cavamax® W7 (β-cyclodextrin), Captisol® (sulfoalkyl ether-β-cyclodextrin), Cavasol® W7 M (methyl-β-cyclodextrin), Cavasol® W8 HP (hydroxypropyl-γ-cyclodextrin), Cavamax® W8 (γ-cyclodextrin), Cavamax® W6 (α-cyclodextrin).

In one embodiment, the cyclodextrin is 2-hydroxypropyl-β-cyclodextrin (HP-β-CD), which is a cyclic oligosaccharide containing seven D-(+)-glucopyranose units.

Stabilizers increase stability of netupitant in the chosen pharmaceutical acceptable vehicle. The stabilizer may be selected from, but are not limited to, inorganic acids such as hydrochloric acid, hydrobromic acid, sulfuric acid, nitric acid, phosphoric acid and the like, and organic acids such as adipic acid, acetic acid, ascorbic acid, aspartic acid, benzoic acid, cinnamic acid, glutamic acid, glycolic acid, citric acid, succinic acid, tartaric acid, lactic acid, fumaric acid, maleic acid, malic acid, malonic acid, mandelic acid, methane sulfonic acid, ethane sulfonic acid, propionic acid, pyruvic acid, toluene sulfonic acid, salicylic acid and oxalic acid and combinations thereof. The amount of stabilizer may range from about 0.1 mg/mL to about 250 mg/mL of the composition, and preferably from about 0.5 mg/mL to about 200 mg/mL.

In some embodiments of the present invention, pharmaceutical compositions may contain buffering agents, which are used to resist change in pH upon dilution or addition of acid or alkali. Such compounds include, by way of example and without limitation, sodium dihydrogen phosphate monohydrate, disodium hydrogen phosphate anhydrous, benzoic acid, sodium benzoate, monobasic sodium phosphate, dibasic sodium phosphate, disodium hydrogen phosphate dodecahydrate, tromethamine (TRIS buffer), potassium metaphosphate, potassium phosphate, monobasic sodium acetate, sodium bicarbonate, sodium carbonate, potassium carbonate, sodium tartrate and others known to those of ordinary skill in the art. The amount of buffering agent may range from about 0.1 mg/mL to about 50 mg/mL of the composition, and preferably from about 0.5 mg/mL to about 25 mg/mL.

In some embodiments of the present invention, pharmaceutical compositions may contain "tonicity contributing agent" that can be used to adjust the tonicity of the liquid formulation. Suitable tonicity agents include glycerine, lactose, mannitol, dextrose, sodium chloride, sodium sulphate, sorbitol, trehalose, xylitol, sucrose, maltose, and others known to those or ordinary skill in the art. In one embodiment, the tonicity of the liquid formulation approximates that of the tonicity of blood or plasma. The amount of tonicity agent may range from about 0.1 mg/mL to about 20 mg/mL of the composition, preferable from about 5 to about 10 mg/mL.

In some embodiments of the present invention, pharmaceutical compositions may contain chelating agent selected from the group consisting of ethylene-diamine tetra acetic acid (EDTA), diethylenetriaminepentaacetic acid (DTPA), ethylene glycol-bis (β-aminoethyl ether)-tetra acetic acid (EGTA), N-(hydroxyethyl) ethylene-diaminetriacetic acid (HEDTA), nitrilotriacetic acid (NTA), triethanolamine, 8-hydroxyquinoline, gluconic acid, saccharic acid, thiodipropionic acid, acetonic dicarboxylic acid, lecithin, di(hydroxyethyl)glycine, phenylalanine, tryptophan, glycerine, sorbitol and pharmaceutically acceptable salts thereof. More preferably, the chelating agent is selected from the group consisting of EDTA, DTPA, gluconic acid or a pharmaceutically acceptable salt thereof. The amount of chelating agent may range from about 0.1 mg/mL to about 50 mg/mL of the composition, and preferably from about 0.5 mg/mL to about 25 mg/mL.

In some embodiments of the present invention, a stable solution suitable for parenteral administration comprises: (a) netupitant (b) palonosetron hydrochloride, (c) stabilizer, (d) solubilizer, and (e) a vehicle, wherein said solution does not contain chelating agent.

In some embodiments of the present invention, pharmaceutical compositions may contain an antioxidant which inhibits oxidation and thus is used to prevent the deterioration of preparations by the oxidative process. Such compounds include by way of example and without limitation sodium bisulfate, sodium ascorbate, ascorbic acid, ascorbyl palmitate, glycine, L-cysteine hydrochloride, L-methionine, butylated hydroxy anisole, butylated hydroxytoluene, hydro phosphorous acid, monothioglycerol, propyl gallate, sodium thiosulfate, sodium sulfide, sodium sulfite, sodium bisulfite, sodium formaldehyde sulfoxylate, thioglycolic acid, sodium metabisulfite and others known to those of ordinary skill in the art. The amount of anti-oxidant may range from about 0.1 mg/mL to about 50 mg/mL of the composition, and preferably from about 0.5 mg/mL to about 25 mg/mL.

In some embodiments of the present invention, pharmaceutical compositions may contain a preservative. Suitable preservative may be selected from the group consisting of ethanol, benzoic acid and the sodium or potassium salts thereof, sorbic acid and the sodium or potassium salts thereof, chlorobutanol, benzyl alcohol, phenyl ethanol, methyl, ethyl, propyl or butyl-p-hydroxybenzoates, phenol, m-cresol, p-chloro-m-cresol, phenylmercury nitrate, benzalkonium chloride and mixtures thereof. The amount of preservative may range from about 0.1 mg/mL to about 50 mg/mL of the composition, and preferably from about 0.5 mg/mL to about 25 mg/mL.

The pH of the pharmaceutical composition preferably ranges from about 2.0 to about 6 when measured at room temperature. In some embodiments, the pH of the solutions of the composition ranges from about 2.5 to about 6.0, about 3.0 to about 6.0, about 3.5 to about 6, about 4.0 to about 6.0, about 2.0 to about 5.5, about 2.0 to about 5, or about 2.0 to about 4.5.

In some embodiments of the present invention, pharmaceutical compositions may contain pH adjusting agents. The pH adjusting agents may be selected from the group consisting of sodium hydroxide, potassium hydroxide, magnesium hydroxide, tromethamine, sodium linoleate, sodium oleate, potassium linoleate, potassium oleate, diethanolamine and mixtures thereof. In some embodiments, pharmaceutical composition comprising netupitant can be formulated by using any suitable pH adjusting agent. In some embodiments, it is possible to maintain the pH of the composition without using a suitable buffering agent.

In particular, the compositions of present invention provides netupitant in a concentration of about 0.5 mg/mL, about 1.0 mg/mL, about 1.5 mg/mL, about 2.0 mg/mL, about 2.5 mg/mL, about 3.0 mg/mL, about 3.5 mg/mL, about 4.0 mg/mL, about 4.5 mg/mL, about 5.0 mg/mL, about 5.5 mg/mL, about 6.0 mg/mL, about 6.5 mg/mL, about 7.0 mg/mL, about 7.5 mg/mL, about 8.0 mg/mL, about 8.5 mg/mL, about 9.0 mg/mL, about 9.5 mg/mL, about 10.0 mg/mL, about 10.5 mg/mL, about 11.0 mg/mL, about 11.5 mg/mL, about 12.0 mg/mL, about 12.5 mg/mL, about 13.0 mg/mL, about 13.5 mg/mL, about 14.0 mg/mL, about 14.5 mg/mL, about 15.0 mg/mL, about 15.5 mg/mL, about 16.0 mg/mL, about 16.5 mg/mL, about 17.0 mg/mL, about 17.5 mg/mL, about 18.0 mg/mL, about 18.5 mg/mL, about 19.0 mg/mL, about 19.5 mg/mL, about 20.0 mg/mL, about 20.5 mg/mL, about 21.0 mg/mL, about 21.5 mg/mL, about 22.0 mg/mL, about 22.5 mg/mL, about 23.0 mg/mL, about 23.5 mg/mL, about 24.0 mg/mL, about 24.5 mg/mL, about 25.0 mg/mL, about 25.5 mg/mL, about 26.0 mg/mL, about 26.5 mg/mL, about 27.0 mg/mL, about 27.5 mg/mL, about 28.0 mg/mL, about 28.5 mg/mL, about 29.0 mg/mL, about 29.5 mg/mL and about 30.0 mg/mL.

The unit dosage form contains an amount netupitant ranging from about 1 mg to about 500 mg. Exemplary unit doses of netupitant range from about 10 mg to about 250 mg, including unit dosages of about 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 232.5 mg, 235 mg, 237.5 mg, 240 mg, 242.5 mg, 245 mg, 250 mg, 300 mg, 350 mg, 400 mg, 450 mg and 500 mg, wherein unit dose may be packed in a vial, ampoule, pre-filled syringe, cartridge or auto-injector.

Concentration of palonosetron in the solution may be about 0.001 mg/mL or more. In particular, the compositions of present invention provides palonosetron in a concentration of about 0.001 mg/mL, about 0.002 mg/mL, about 0.003 mg/mL, about 0.004 mg/mL, about 0.005 mg/mL, about 0.006 mg/mL, about 0.006 mg/mL, about 0.007 mg/mL, about 0.008 mg/mL, about 0.009 mg/mL, about 0.01 mg/mL, about 0.011 mg/mL, about 0.012 mg/mL, about 0.013 mg/mL, about 0.014 mg/mL, about 0.015 mg/mL, about 0.016 mg/mL, about 0.017 mg/mL, about 0.018 mg/mL, about 0.019 mg/mL, about 0.020 mg/mL, about 0.021 mg/mL, about 0.022 mg/mL, about 0.023 mg/mL, about 0.024 mg/mL, about 0.025 mg/mL, about 0.026 mg/mL, about 0.027 mg/mL, about 0.028 mg/mL, about 0.029 mg/mL, about 0.030 mg/mL, about 0.031 mg/mL, about 0.032 mg/mL, about 0.033 mg/mL, about 0.034 mg/mL, about 0.035 mg/mL, about 0.036 mg/mL, about 0.037 mg/mL, about 0.038 mg/mL, about 0.039 mg/mL, about 0.04 mg/mL, about 0.05 mg/mL, about 0.06 mg/mL, about 0.07 mg/mL, about 0.08 mg/mL, about 0.09 mg/mL, and about 0.1 mg/mL.

Exemplary unit dose of palonosetron range from 0.10 mg to 0.7 mg, including unit dosages of about 0.01 mg, 0.02 mg, 0.03 mg, 0.04 mg, 0.05 mg, 0.06 mg, 0.07 mg, 0.07 mg, 0.08 mg, 0.09 mg, 0.1 mg, 0.12 mg, 0.13 mg, 0.14 mg, 0.15 mg, 0.16 mg, 0.17 mg, 0.18 mg, 0.19 mg, 0.2 mg, 0.21 mg, 0.22 mg, 0.23 mg, 0.24 mg, 0.25 mg, 0.26 mg, 0.27 mg, 0.28 mg, 0.29 mg, 0.3 mg, 0.31 mg, 0.32 mg, 0.33 mg, 0.34 mg, 0.35 mg, 0.36 mg, 0.37 mg, 0.38 mg, 0.39 mg, 0.4 mg, 0.41 mg, 0.42 mg, 0.43 mg, 0.44 mg, 0.45 mg, 0.46 mg, 0.47 mg, 0.48 mg, 0.49 mg, 0.5 mg, 0.51 mg, 0.52 mg, 0.53 mg, 0.54 mg, 0.55 mg, 0.56 mg, 0.57 mg, 0.58 mg, 0.59 mg, 0.6 mg, 0.61 mg, 0.62 mg, 0.63 mg, 0.64 mg, 0.65 mg, 0.66 mg, 0.67 mg, 0.68 mg, 0.69 mg and 0.7 mg wherein unit dose may be packed in a vial, ampoule, pre-filled syringe, cartridge or auto-injector.

The finished products may be sterilized by any suitable method, e.g., aseptic filtration-filling-sealing, terminal sterilization, incorporation of sterilizing agents, irradiation, and/or heating.

Sterilization may be accomplished by any of the conventional methods including aseptic filling, irradiation, and heat sterilization. Heat sterilization is normally performed using steam, preferably wet steam to allow for the use of pressure as a means of temperature control. The time period for the sterilization must be long enough to meet the sterility requirements required of an injectable product. When steam is used, the period may be from about 5 to 30 minutes at temperatures of about 110° C. to 130° C., or from about 10 to 30 minutes at temperatures of about 110° C. to 130° C., preferably at 120° C. to 125° C. for 15 to 30 minutes. In another embodiment, the sterilization can be at 120° C. for 5 to 15 minutes.

A pharmaceutically inert gas may be bubbled into the solution to drive out oxygen, which may be selected from nitrogen or carbon dioxide. Preferably, the solution is kept under nitrogen or carbon dioxide sparging until dissolved oxygen is less than 10 mg/L in the final solution.

Containers suitable according to the present invention are those known in the art. They include vials, cartridges, pre-filled syringes, auto-injectors, infusion bags, bottles, and ampoule presentations. Containers may be fabricated from glass or from polymeric materials. Suitable containers should be of a size sufficient to hold one or more doses of netupitant.

In some embodiment of the present invention, stable injectable solution comprising netupitant alone or in combination with palonosetron is filled in single-dose and/or multi-dose containers. In some embodiments, the solution may be contained in a vial. In some embodiments, the vial may be made from clear glass, amber glass, or plastic. In some embodiments, the vial or pre-filled syringe may be in the range of about 0.1 mL to 100 mL in volume, preferably in the range of about 1 mL to 50 mL, more preferably in the range of about 1 mL to 20 mL. In some embodiments, the same vial may be used for multiple applications of the solution for up to about 10 days after initial use, preferably up to about 15 days, more preferably up to about 30 days, more preferably up to about 45 days, and most preferably up to about 60 days.

In some embodiments, the invention provides ready-to-dilute solution in a vial having 13 mL or 15 mL fill volumes comprising 197 mg of netupitant and 0.28 mg of palonosetron. In other embodiments, the invention provides ready-to-use solution in a vial or infusion bag having 50 mL, 100 mL or 200 mL fill volumes comprising 197 mg of netupitant and 0.28 mg of palonosetron. In another embodiment, the present invention relates to vial, ampoule or syringe which is dimensioned to have a nominal maximum fill volume of between about 1 mL and about 250 mL.

The polymeric materials which may be used include: polysulfone, polycarbonate, polypropylene, polyethylene (LDPE or HOPE), ethylene/propylene copolymers, polyolefins, acrylic-imide copolymers, polyester (e.g., PET, PEN and the like), Teflon, Nylon, acetal (Delrin), polymethyl pentene, PVDC, ethylvinylacetate, AN-copolymer etc. In addition, crystal zenith (CZ) resin containers and similar resins can be used as rigid containers and syringes.

Stability: As used herein, the term "stable" refers to chemical stability, wherein no more than about 10% loss of netupitant under typical commercial storage conditions. In certain embodiments, the compositions of the present invention will have no more than about 5% loss of netupitant, more preferably, no more than about 2% loss of netupitant, under typical commercial storage conditions. The composition retains at least about 95% of the potency of netupitant after storing the composition at 40° C. and 75% relative humidity (herein after mentioned as RH) for at least three months.

In certain embodiments, the term "stable" means that not more than 10% w/w of total related substances are formed on storage at accelerated conditions of stability at 40° C. and 75% RH, or at 25° C. and 60% RH, or 2-8° C. for a period of at least 3 months or 6 months or 12 months or 24 months.

The term "physically stable" as used herein, means the pharmaceutical composition in the form of a solution of the present invention does not show any sign of crystallization, precipitation or haziness upon storage or after dilution with suitable diluent.

The present pharmaceutical composition in the form of a solution is stable physically and chemically at 40° C./75% RH or at 25° C./60% RH or 2-8° C. for a period of at least two months. It was indeed surprising to find that even after addition with a sufficient amount of diluent, the compositions of the invention remained physically stable in the form of a solution without any precipitation.

In certain embodiments of the present invention, the stable injectable solution comprising netupitant alone or in combination with palonosetron is stable for at least 6 months at 25° C./60% RH or 40° C./75% RH condition.

In some embodiments, the Netupitant-N-Oxide Impurity (i.e., 4-(4-Chlorophenyl)-2-pyrrolidinone) may be monitored. The structure of N-Oxide impurity is shown below:

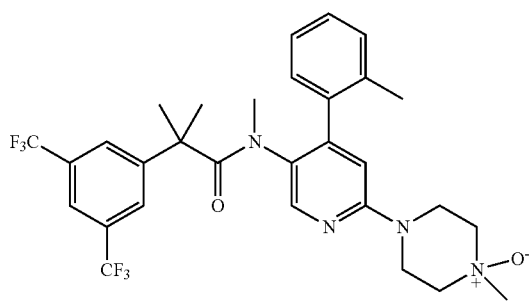 [SMILES: Cc1ccccc1-c1cc(N2CC[N+](C)([O-])CC2)ncc1N(C)C(=O)C(C)(C)c1cc(C(F)(F)F)cc(C(F)(F)F)c1]

Netupitant-N-Oxide Impurity

In some embodiments, the Palonosetron Impurity-D (i.e., (3aR)-2-[(3S)-Quinuclidin-3-yl]-2,3,3a,4,5,6-hexahydro-1H-benzo[de]isoquinolin-1-one hydrochloride) may be monitored. The structure of Palonosetron Impurity-D is shown below:

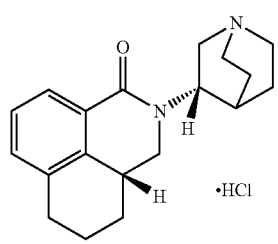 [SMILES: O=C1c2cccc3c2[C@@H](CCC3)CN1[C@@H]1CN2CCC1CC2 ; Cl]

(3aR)-2-[(3S)-Quinuclidin-3-yl]-2,3,3a,4,5,6-hexahydro-1H-benzo[de]isoquinolin-1-one Hydrochloride In some embodiments, the Palonosetron Impurity-E (i.e., 2-[(3S)-Quinuclidin-3-yl]-2,4,5,6-tetrahydro-1H-benzo[de]isoquinolin-1-one hydrochloride) may be monitored. The structure of Palonosetron Impurity-E is shown below:

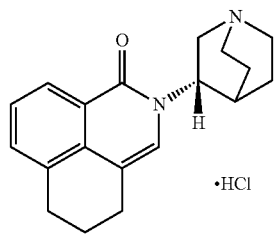 [SMILES: O=c1c2cccc3c2c(cn1[C@@H]1CN2CCC1CC2)CCC3 ; Cl]

2-[(3S)-Quinuclidin-3-yl]-2,4,5,6-tetrahydro-1H-benzo[de]isoquinolin-1-one Hydrochloride In some embodiments of the present invention, the stable injectable solution comprising netupitant alone or in combination with palonosetron was found to remain as a clear solution on storage and after dilution, without any recrystallization or precipitation, when stored for at least 6 months at 2-8° C., 25° C./60% RH condition, or 40° C./75% RH condition.

In an embodiment of the present invention, the stable injectable solution comprising netupitant alone or in combination with palonosetron, does not contain a single unknown impurity of more than 1%, and/or does not contain total impurities of more than 3% (for example, not more than 2%, 1%, or 0.5%), after storage for more than 2 months, for example, for 3 months, for 6 months, for 12 months, for 18 months, for 24 months or for 36 months when stored at (i) 2-8° C. temperature, (ii) 25±2° C. temperature and 60±5% RH, or (iii) 40±2° C. and 75±5% RH. The parenteral solution comprising netupitant of the present invention does not form any precipitate and remains physically stable after storage for more than 2 months, for example, for 3 months, for 6 months, for 12 months, for 18 months, for 24 months or for 36 months when stored at 2-8° C. temperature or at 25±2° C. temperature and 60±5% RH.

In another embodiment of the present invention, the stable injectable solution comprising netupitant alone or in combination with palonosetron has a shelf-life in a sealed original packaging of about 1 month or more, between 1 month and 36 months, but at least between 1 month and 24 months, or preferably between 1 month and 12 months.

Dosage and Administration: The inventive pharmaceutical compositions as described herein may be used in treating nausea and vomiting, wherein therapeutically effective amount of netupitant and palonosetron are administered to a human subject.

For administration to human subjects, the present application provides pharmaceutical compositions comprising an effective amount of netupitant and palonosetron. The formulation may be prepared using conventional methods, for example, depending on the subject to be treated, the mode of administration, and the type of treatment desired (e.g., prevention, prophylaxis, or therapy).

Preferably, the present application relates to method for managing or treating or preventing nausea and vomiting, alone or in combination with corticosteroids, the method comprising administering the human subject, a pharmaceutical composition comprising netupitant and palonosetron.

In another embodiment, the invention provides methods of treating emesis by administering one or more of the dosage forms described herein. The dosage form is preferably administered shortly before the emesis inducing event (i.e., no more than 2 hours before the event). The emesis may be acute phase emesis (i.e., emesis experienced within about 24 hours of an emesis inducing event), or delayed emesis (i.e., emesis experienced after the acute phase, but within seven, six, five or four days of an emesis inducing event). The emesis may constitute CINV, from moderately or highly emetogenic chemotherapy, RINV or PONV.

In still other embodiments the present invention provides methods of treating acute and delayed-onset emesis by administering the dosage forms of the present invention to a human in need thereof, preferably shortly before the emesis inducing event.

In an embodiment, the present invention provides a method of treating nausea and vomiting for a period of five consecutive days in a patient in need thereof, comprising administering to the patient netupitant alone or in combination with palonosetron in an amount which is therapeutically effective against nausea and vomiting during the acute and delayed phases, and which is effective to enter the systemic circulation, cross the blood brain barrier and occupy at least 70% of NK-1 receptors in the striatum seventy-two hours after said administration.

The methods of the present invention are all effective at treating or preventing nausea and vomiting induced by numerous events, including chemotherapy induced nausea and vomiting ("CINV"), from moderately or highly emetogenic chemotherapy, radiation therapy induced nausea and vomiting ("RINV"), and post-operative nausea and vomiting ("PONV"). The method is preferably performed shortly before the emesis inducing event (i.e., no more than 1 or 2 hours before the event). The methods may be used to treat nausea and vomiting during the acute phase of emesis, or during the delayed phase.

Acute emesis refers to the first twenty-four-hour period following an emesis-inducing event. Delayed emesis refers to the second, third, fourth and fifth twenty-four-hour periods following an emesis-inducing event. When a treatment is said to be effective during the delayed phase, it will be understood to mean that the effectiveness of the treatment is statistically significant during the entire delayed phase, regardless of whether the treatment is effective during any twenty-four-hour period of the delayed phase. It will also be understood that the method can be defined based upon its effectiveness during any one of the twenty-four-hour periods of the delayed phase. Thus, unless otherwise specified, any of the methods of treating nausea and/or vomiting during the delayed phases, as described herein, could also be practiced to treat nausea and/or vomiting during the second, third, fourth or fifth twenty-four-hour periods following an emesis inducing event, or a combination thereof.

Determination of netupitant and palonosetron optimal dosage may require individual titration. Therapy may be started at a low dosage and increased gradually until optimum effect is achieved (e.g., usually between 50-300 mg of netupitant and 0.10 mg to 0.75 mg of palonosetron). In certain embodiments, 1-20 mL of netupitant and palonosetron solution may be administered intravenously to achieve optimum effect, preferably 10-15 mL may be administered to achieve optimum effect.

In an embodiment, the present invention relates to a method of preventing or managing or treating or alleviating acute and delayed nausea and vomiting associated with initial and repeat courses of cancer chemotherapy in a subject, especially a human subject, the method comprising administering 197.5 mg of netupitant and 0.25 mg of palonosetron solution, intravenously over 30-60 minutes.

In one embodiment of the method as disclosed herein, the intravenous dose (including a bolus dose) of netupitant and palonosetron solution is administered to the patient over the course of about 10 to about 60 minutes, including all values and sub-ranges there between.

The drugs specified by the individual embodiments may be administered by any suitable dosing regimen, as is well known in the art, but in a preferred embodiment the netupitant, 5-HT3 antagonist are administered parenterally and corticosteroids are administered orally. A preferred dose of palonosetron ranges from about 0.075 to about 1.0 mg, or from about 0.25 to about 0.75 mg, but is preferably about 0.25 mg. A preferred dose of netupitant ranges from about 50 to 500 mg, or from about 200 to about 400 mg, but is preferably about 197.5 mg. A preferred dose of corticosteroid, preferably dexamethasone, is 12 mg administered orally or via injection on the first day of treatment, and 8 mg administered orally or via injection on the second, third and fourth days after said treatment.

In some embodiments, the methods comprise administering stable injectable solutions comprising netupitant alone or in combination of palonosetron to a subject at about 24 hours, at about 48 hours, at about 72 hours, at about 96 hours, at about 120 hours, at about 144 hours, and so forth after the first dose of netupitant administered to the subject.

In one embodiment, the methods disclosed herein comprise administering to the patient a dose of netupitant intravenously, wherein the netupitant is at a dose of about 197.5 mg. In some embodiments, the methods disclosed herein comprise administering to the patient a dose of netupitant intravenously, wherein the netupitant is at a concentration of about 15.2 mg/mL.

In certain aspects, the inventive pharmaceutical compositions described herein may be used to treat adults and adolescents (e.g., about 13-17 years). In certain aspects, the pharmaceutical compositions described herein may be used as monotherapy or as adjunctive therapy. For example, additional active agents may be used in adjunctive therapy with netupitant, such as corticosteroids and 5-HT3 antagonists (e.g., dexamethasone, prednisolone etc.).

EXAMPLES

The following examples are exemplary and not intended to be limiting. The above disclosure provides many different embodiments for implementing the features of the invention, and the following examples describe certain embodiments. It will be appreciated that other modifications and methods known to one of ordinary skill in the art can also be applied to the following experimental procedures, without departing from the scope of the invention.

General HPLC Procedure

As explained in detail below, the following HPLC procedure can be used for assay of Netupitant. The materials and general conditions are listed below:

Chromatographic Conditions

TABLE 1

| | |
|---|---|
| Column | Agilent Zorbax ® C8, 250 × 4.6 mm, 5μ |
| Column Temperature | 40° C. |
| Sample temperature | 10° C. |
| Flow rate | 1.0 mL/min |
| Detector | 210 nm with PDA/UV detector |
| Injection volume | 10 μL |
| Run time | 30 minutes |
| Mobile Phase A | Pipette out and transfer 1 mL of Trifluoro acetic acid to 1000 mL of water, mix well. |
| Mobile Phase B | Prepare a mixture of acetonitrile and water in 90:10 v/v ratio. |

Gradient Program

TABLE 2

| Time (min) | % Mobile phase-A | % Mobile phase-B |
|---|---|---|
| 0 | 60 | 40 |
| 5.0 | 60 | 40 |
| 15.0 | 15 | 85 |
| 20.0 | 15 | 85 |
| 21.0 | 60 | 40 |
| 30.0 | 60 | 40 |

The following HPLC procedure can be used for assay of palonosetron. The materials and general conditions are listed below:

Chromatographic Conditions

TABLE 3

| | |
|---|---|
| Column | Agilent Zorbax ® C8, 250 × 4.6 mm, 5μ |
| Column Temperature | 25° C. |
| Sample temperature | 20° C. |
| Flow rate | 1.0 mL/min |
| Detector | 210 nm with PDA/UV detector |
| Injection volume | 40 μL |
| Run time | 50 minutes |
| Mobile Phase A | Pipette out and transfer 1 mL of Trifluoro acetic acid to 1000 mL of water, mix well. |
| Mobile Phase B | Prepare a mixture of acetonitrile and water in 90:10 v/v ratio. |

Gradient Program

TABLE 4

| Time (min) | % Mobile phase-A | % Mobile phase-B |
|---|---|---|
| 0 | 90 | 10 |
| 5.0 | 90 | 10 |
| 30.0 | 50 | 50 |
| 32.0 | 10 | 90 |
| 40.0 | 10 | 90 |
| 41.0 | 90 | 10 |
| 50.0 | 90 | 10 |

The following HPLC procedure can be used to detect and quantify impurities of Netupitant. The materials and general conditions are listed below:

Chromatographic Conditions

TABLE 5

| | |
|---|---|
| Column | Kromasil ® 100-5-C18, 250 × 4.6 mm, 5μ |
| Column Temperature | 35° C. |
| Sample temperature | 10° C. |
| Flow rate | 1.0 mL/min |
| Detector | 257 nm with PDA/UV detector |
| Injection volume | 10 μL |
| Run time | 80 minutes |
| Mobile Phase A | Dissolve 1.72 g of Di-potassium hydrogen phosphate in 1000 mL of water, add 2 mL trimethylamine and adjust the pH of solution to 6.0 ± 0.05 with o-phosphoric acid. |
| Mobile Phase B | Prepare a mixture of acetonitrile and water 90:10% v/v ratio. |

Gradient Program

TABLE 6

| Time (min) | % Mobile phase-A | % Mobile phase-B |
|---|---|---|
| 0.01 | 70 | 30 |
| 8 | 70 | 30 |
| 30 | 30 | 70 |
| 60 | 10 | 90 |
| 70 | 5 | 95 |
| 71 | 70 | 30 |
| 80 | 70 | 30 |

The following HPLC procedure can be used to detect and quantify impurities of palonosetron. The materials and general conditions are listed below:

Chromatographic Conditions

TABLE 7

| | |
|---|---|
| Column | Zorbax eclipse plus phenyl hexyl 250 × 4.6 mm, 5μ |
| | Kinetex biphenyl 250 × 4.6 mm, 5μ |
| Column Temperature | 25° C. |
| Sample temperature | 20° C. |
| Flow rate | 0.8 mL/min & 1.0 mL/min |
| Detector | 210 nm with PDA/UV detector |
| Injection volume | 100 μL |
| Run time | 180 minutes |
| Mobile Phase A | Dissolve 2.72 g of 1-Decane sulfonic acid sodium salt monohydrate in 1000 mL of water, add 1 mL Perchloric acid and mix well. |
| Mobile Phase B | Prepare a mixture of acetonitrile and Mobile phase-A 90:10% v/v ratio. |

Gradient Program

TABLE 8

| Time (min) | Flow (mL/min) | % Mobile phase-A | % Mobile phase-B |
|---|---|---|---|
| 0.01 | 0.8 | 70 | 30 |
| 50 | 0.8 | 65 | 35 |
| 90 | 0.8 | 60 | 40 |
| 105 | 0.8 | 60 | 40 |
| 107 | 1.0 | 0 | 100 |
| 142 | 1.0 | 0 | 100 |
| 145 | 0.8 | 70 | 30 |
| 180 | 0.8 | 70 | 30 |

Experiment 1

TABLE 9

| Ingredients | Composition A |
| --- | --- |
| Netupitant | 197 mg |
| Ethanol | 8 gm |
| Citric Acid | 150 mg |
| Maleic Acid | 0.2 mg |
| Water for injection | Q.S. to 10 mL |

Manufacturing Procedure:
1. About 50% of required quantity of water for injection was taken in a beaker and specified quantities of citric acid and maleic acid were added to the water for injection and stirred for about 10 minutes at 300 RPM to obtain a clear aqueous solution.
2. Required quantity of ethanol was taken in a separate Duran bottle and specified quantity of netupitant was added into the bottle and stirred for about 10 minutes at 300 RPM to obtain ethanolic solution.
3. The aqueous solution was added to the ethanolic solution under continuous stirring for 10 minutes at 300 RPM to get a solution.
4. The above final solution was diluted with 0.9% NaCl and 5% dextrose solutions to obtain a final mixture having a netupitant concentration of 3.94 mg/mL. However, it was observed that netupitant had precipitated out from the solution upon dilution.

Experiment 2

TABLE 10

| Ingredients | Composition B | Composition C | Composition D |
| --- | --- | --- | --- |
| Netupitant | 197.5 mg | 197.5 mg | 197.5 mg |
| Polysorbate 80 | 300 mg | 1.5 mg | 3 mg |
| Ethanol | 4.2 gm | 4.5 gm | 3 gm |
| Total fill volume | 4.5 mL | 6 mL | 6 mL |

Manufacturing Procedure:
1. Required quantity of ethanol was taken in a Duran bottle and specified quantity of netupitant was added into bottle and stirred for about 10 minutes at 300 RPM to obtain an ethanolic solution.
2. Specified quantity of polysorbate 80 was added to the ethanolic solution and stirred until a clear solution was obtained.
3. The above solution was diluted with 0.9% NaCl and 5% dextrose solutions to get a final mixture with a netupitant concentration of 3.95 mg/mL.
4. However, it was observed that upon dilution the final mixture of composition B was a hazy solution, that of composition C had precipitated within 10 minutes, and while the mixture of composition D was clear for the first 2 hours, it had started precipitating after 2 hours.

Experiment 3

TABLE 11

| Ingredients | Composition E | Composition F | Composition G | Composition H |
| --- | --- | --- | --- | --- |
| Netupitant | 197.5 mg | 197.5 mg | 197.5 mg | 197.5 mg |
| Ethanol | 3.0 gm | 3.0 gm | 3.0 gm | 3.0 gm |
| Polysorbate 80 | 4.5 mg | 4.5 mg | 4.5 mg | 4.5 mg |
| Maleic acid | 1.0 mg | 1.0 mg | — | 1.0 mg |
| Phosphoric acid | — | — | 200 mg | 200 mg |
| Propylene Glycol | — | 2.25 gm | — | 2.25 gm |
| Total fill volume | 7.5 mL | 9.75 mL | 7.5 mL | 10 mL |

Manufacturing Procedure:

1. Required quantity of ethanol was taken in a Duran bottle and specified quantity of netupitant was added to bottle and stirred for about 10 minutes at 300 RPM to obtain ethanolic solution.
2. Specified quantity of polysorbate 80 was added to the ethanolic solution and stirred to get a clear solution.
3. Specified quantity of propylene glycol was added to the solution obtained in step 2 and stirred until a clear solution was obtained.
4. Specified quantity of maleic acid and/or phosphoric acid was added to the solution obtained in step 3 and stirred for 10 minutes to get a clear solution.
5. The above solution from step 4 was diluted with 5% dextrose solutions to get a final netupitant concentration of 3.95 mg/mL. At this stage the solutions of compositions E & F were clear for up to 2 hours but started precipitating thereafter; composition G was stable for up to 24 hours but started precipitating after 24 hours; and the solution of composition H was clear up to 28 hours.
6. The above diluted solutions of compositions E, F & H from step 5 were further diluted with 5% dextrose solutions to get a final netupitant concentration of 1.975 mg/mL. At this stage, it was observed that the solution of compositions E and F were clear for up to about 2 hours but started precipitating after 2 hours. The final solution of composition H remained clear for 28 hours.

Experiment 4

TABLE 12

| Ingredients | Composition I | Composition J | Composition K | Composition L |
|---|---|---|---|---|
| Netupitant | 197.5 mg | 197.5 mg | 197.5 mg | 197.5 mg |
| Ethanol | 3 gm | 3 gm | 3 gm | 3 gm |
| Polysorbate 80 | 4.5 mg | 4.5 mg | 4.5 mg | 2.5 mg |
| TRIS | 100 mg | — | 100 mg | 100 mg |
| Phosphoric acid | 200 mg | 60 mg | 60 mg | 200 mg |
| Propylene glycol | 1 gm | 11 gm | 1 gm | 1 gm |
| Milli-Q water | 1.5 mL | 1.5 mL | 1.5 mL | 4.5 mL |
| Total fill volume | 10 mL | 10 mL | 10 mL | 11 mL |
| pH after $1^{st}$ dilution | 2.60 | 2.60 | — | 2.65 |
| pH after $2^{nd}$ dilution | 2.54 | 2.55 | — | |
| Appearance before dilution | Clear | Clear | Hazy | Clear |

Manufacturing Procedure:
1. Required quantity of ethanol was taken in a Duran bottle and specified quantity of netupitant was added to ethanol and stirred for about 10 minutes at 300 RPM to obtain a clear ethanolic solution.
2. Specified quantity of polysorbate 80 was added to the ethanolic solution and stirred to get a clear solution. Further, specified quantity of propylene glycol was added and stirred to get a clear solution.
3. Required quantity of Milli-Q water was taken in a beaker and specified quantity of phosphoric acid was added and stirred for 5 minutes to form clear phosphoric acid solution. Specified quantity of TRIS was added to phosphoric acid solution and stirred for 5 minutes to form a clear solution.
4. The above solution obtained after step 3 was added to the ethanolic solution obtained after step 2 and stirred for 10 minutes to obtain a clear solution.
5. The solution of step 4 was diluted with 5% dextrose solution to get a solution with netupitant concentration of 3.95 mg/mL. pH of the obtained solution was measured and recorded in Table 12. The diluted compositions I, J & L remained clear for up to 28 hours.
6. The above diluted netupitant solution of step 5 were further diluted with 0.9% NaCl or 5% dextrose solution to get a final netupitant concentration of 1.975 mg/mL. pH of the obtained solution was measured and recorded in Table 12. The further diluted compositions I, J & L remained clear for up to 28 hours.

Experiment 5

TABLE 13

| Ingredients | Composition M |
|---|---|
| Netupitant | 197.5 mg |
| Ethanol | 3 gm |
| Polysorbate 80 | 2.5 mg |
| TRIS | 100 mg |
| Phosphoric acid | 200 mg |
| Propylene glycol | 1 gm |
| Meglumine | 200 mg |
| Water for Injection | 4.5 mL |
| Total fill volume | 11 mL |
| Final pH | 6.5 |

Manufacturing Procedure:
1. Required quantity of ethanol was taken in a Duran bottle and specified quantity of netupitant was added to ethanol and stirred for about 10 minutes at 300 RPM to obtain an ethanolic solution.
2. Specified quantity of polysorbate 80 was added to the ethanolic solution and stirred to get a clear solution. Specified quantity of propylene glycol was then added to that solution and stirred to get a clear ethanolic solution.
3. Required quantity of water was taken in a beaker and specific quantity of phosphoric acid was added and stirred for 5 minutes to form a clear phosphoric acid solution. Specified quantities of TRIS and meglumine were added to the phosphoric acid solution and stirred for 5 minutes to form a clear solution.
4. The above solution from step 3 was added to ethanolic solution of step 2 and stirred for 10 minutes to obtain a clear solution. pH of the obtained solution was measured and recorded in Table 13.
5. The solution of step 4 was diluted with 5% dextrose solution to get a final netupitant concentration of 3.95 mg/mL. This diluted netupitant solution was clear up to 24 hours and precipitated after 24 hours.

Experiment 6

TABLE 14

| Ingredients | Composition N |
|---|---|
| Netupitant | 197.5 mg |
| Ethanol | 3 gm |
| Polysorbate 80 | 2.5 mg |
| TRIS | 100 mg |
| Phosphoric acid | 200 mg |
| Propylene glycol | 1 gm |
| Water for Injection | 3.5 mL |
| Total fill volume | 10 mL |

Manufacturing Procedure:
1. Required quantity of ethanol was taken in a Duran bottle and specified quantity of netupitant was added to ethanol and stirred for about 10 minutes at 300 RPM to obtain an ethanolic solution.
2. Specified quantity of polysorbate 80 was added to the ethanolic solution and stirred to get a clear solution. Specified quantity of propylene glycol was then added and stirred to get a clear solution.
3. Required quantity of water was taken in a beaker and specified quantity of phosphoric acid was added and stirred for 5 minutes to form a clear phosphoric acid solution. Specified quantity of TRIS was added to the phosphoric acid solution and stirred for 5 minutes to form a clear solution.
4. The above solution of step 3 was added to the solution of step 2 and stirred for 10 minutes to obtain a clear solution. The pH of the so obtained liquid composition N was adjusted to different pH values of 3.05, 4.15, 5.35, 5.97, 7.01 & 9.23 with 1N NaOH (sodium hydroxide) solution as recorded in the Table 15 below.
5. The solutions of step 4 were diluted with 5% dextrose solutions to get a final netupitant concentration of 3.95 mg/mL.

TABLE 15

| pH of undiluted solution | 3.05 | 4.15 | 5.35 | 5.97 | 7.01 | 9.23 |
|---|---|---|---|---|---|---|
| Stability | Solution is clear up to 72 hours. | | | | Precipitated after 24 hours. | |
| pH after first dilution | 2.26 | 3.44 | 5.23 | 5.72 | Not performed | |
| Stability | Solution is clear up to 72 hours | | | | | |

Experiment 7

TABLE 16

| Ingredients | Composition O | Composition P | Composition Q |
|---|---|---|---|
| Netupitant | 197.5 mg | 197.5 mg | 197.5 mg |
| Palonosetron HCl | 0.28 mg | 0.28 mg | 0.28 mg |
| Ethanol | 3 gm | 3 gm | 3 gm |
| Polysorbate 80 | 2.5 mg | 2.5 mg | 2.5 mg |
| Phosphoric acid | 200 mg | 150 mg | 150 mg |
| Propylene glycol | 1 gm | 1 gm | 1 gm |
| Water for Injection | 3.5 mL | 3.5 mL | 3.5 mL |
| Total fill volume | 10 mL | 10 mL | 10 mL |
| pH | 6.0 adjusted with NaOH | 5.0 adjusted with NaOH | 5.0 adjusted with Diethanolamine |
| pH after dilution | 5.6 | 4.3 | 4.5 |

Manufacturing Procedure:
1. Required quantity of ethanol was taken in a Duran bottle and specified quantity of netupitant was added to the ethanol and stirred for about 10 minutes at 300 RPM to obtain an ethanolic solution.
2. Specified quantity of polysorbate 80 was added to the ethanolic solution and stirred to get a clear solution. Specified quantity of propylene glycol was then added and stirred to get a clear solution.
3. Required quantity of water was taken in a beaker and specified quantity of phosphoric acid was added and stirred for 5 minutes to form clear phosphoric acid solution. Specified quantity of palonosetron was added to phosphoric acid solution and stirred for 5 minutes to form a clear palonosetron solution.
4. The above palonosetron solution was added to the solution of step 2 and stirred for 10 minutes to get a clear solution. The pH of the so obtained liquid compositions O, P & Q was adjusted to different pH values with 1N NaOH solution or diethanolamine as recorded in the Table 16.
5. The solution of step 4 was diluted with 0.9% NaCl and 5% dextrose solution to get a final netupitant concentration of 3.95 mg/mL. pH of the obtained solution was measured and recorded in Table 16. The compositions O, P & Q so obtained remained clear for up to 24 hours without any precipitation.

Experiment 8

TABLE 17

| Ingredients | Composition R |
|---|---|
| Netupitant | 197.5 mg |
| Ethanol | 3 gm |
| Polysorbate 80 | 2.5 mg |
| Phosphoric acid | 100 mg |
| Propylene glycol | 1 gm |
| Water for Injection | 3.5 mL |
| Total fill volume | 10 mL |
| pH | 6.0 adjusted with NaOH |

Manufacturing Procedure:
1. Required quantity of ethanol was taken in a Duran bottle and specified quantity of netupitant was added to ethanol and stirred for about 10 minutes at 300 RPM to obtain an ethanolic solution.
2. Specified quantity of polysorbate 80 was added to the ethanolic solution and stirred to get a clear polysorbate solution. Specified quantity of propylene glycol was added and stirred to get a clear solution.
3. Required quantity of water was taken in a beaker and specific quantity of phosphoric acid was added and stirred for 5 minutes to form a clear phosphoric acid solution.
4. The above phosphoric acid solution was added to the solution of step 2 and stirred for 10 minutes to get a clear solution. The pH of solution was adjusted with 1N NaOH.
5. The solution of step 4 was diluted with 0.9% NaCl and 5% dextrose solution to get a final netupitant concentration of 3.95 mg/mL. The composition R remained clear for up to 24 hours without any precipitation.

Experiment 9

TABLE 18

| Ingredients | Composition T | Composition U |
|---|---|---|
| Netupitant | 197.5 mg | 197.5 mg |
| Ethanol | 3 gm | 3 gm |
| Polysorbate 80 | 2.5 mg | 2.5 mg |
| Tartaric acid | 65 mg | 65 mg |
| Aspartic acid | 26 mg | 26 mg |
| Palonosetron HCL | 0.28 mg | 0.28 mg |
| Propylene glycol | 1 gm | 1 gm |
| Water for Injection | 6 mL | 6 mL |
| Fill volume | 13 mL | 13 mL |
| pH adjusted with diethanolamine | 4.76 | 5.02 |

Manufacturing Procedure:
1. Required quantity of ethanol was taken in a Duran bottle and specified quantity of netupitant was added to ethanol and stirred for about 10 minutes at 300 RPM to obtain an ethanolic solution.
2. Specified quantity of polysorbate 80 was added to the ethanolic solution and stirred a to get clear polysorbate solution. Specified quantity of propylene glycol was added and stirred to get a clear solution.
3. Required quantity of water was taken in a beaker and specific quantities of tartaric acid and maleic acid were added and stirred for 5 minutes to form an aqueous solution.

4. The aqueous solution was added to the solution of step 2 and stirred for 10 minutes to get a clear solution and pH was adjusted with diethanolamine.
5. The solution of step 4 was diluted with 0.9% NaCl and 5% dextrose solution to get a final netupitant concentration of 3.95 mg/mL. Compositions T and U so obtained remained clear up to 24 hours without any precipitation.

Experiment 10

TABLE 19

| Ingredients | Composition V mg/mL | Composition W mg/mL | Composition X mg/mL |
|---|---|---|---|
| Netupitant | 13.13 | 13.13 | 13.13 |
| Palonosetron HCl | 0.0186 | 0.0186 | 0.0186 |
| Ethanol | 100 | 100 | 100 |
| Polysorbate 80 | 190 | 190 | 190 |
| Citric acid anhydrous | 20 | 20 | 20 |
| Tartaric acid | 1.3 | 1.3 | 1.3 |
| HPβCD | 100 | 100 | 100 |
| Monothioglycerol | 1.66 | — | 1.66 |
| Butylated hydroxytoluene | — | 0.00266 | 0.00266 |
| EDTA | — | 4.36 | — |
| Diethanolamine | pH 5.0 | pH 5.0 | pH 5.0 |
| Water for Injection | q.s. to 1 ml | q.s. to 1 ml | q.s. to 1 ml |

Manufacturing Procedure:
1. Specified quantity of water for Injection was taken in a suitable container and specified quantity of HPβCD was added under stirring until it formed a clear solution.
2. Specified quantity of tartaric acid & citric acid anhydrous were added to step 1 solution under stirring until it formed a clear solution.
3. Specified quantity of polysorbate 80 was added to step 2 solution under continuous stirring.
4. Specified quantity of ethanol was added to step 3 solution.
5. Specified quantity of netupitant was added to step 4 solution under stirring until it formed a clear solution.
6. Specified quantity of monothioglycerol/butylated hydroxytoluene was added to step 5 solution.
7. Specified quantity of palonosetron HCl was added to step 6 solution under stirring until it formed a clear solution.
8. The pH of the above final solution was adjusted to 5.0 by using diethanolamine.
9. Final volume of step 8 solution was made up to 1 ml by using water for injection.

Samples of compositions V, W and X so obtained were stored for 2 weeks @60° C. The solutions remained clear without any precipitation during such storage.

Experiment 11

TABLE 20

| Ingredients | Composition Y mg/mL |
|---|---|
| Netupitant | 13.13 |
| Palonosetron HCl | 0.186 |
| Polysorbate 80 | 190 |
| Tartaric acid | 4.0 |

TABLE 20-continued

| Ingredients | Composition Y mg/mL |
|---|---|
| L-Aspartic acid | 0.12 |
| Citric acid anhydrous | 12.00 |
| HPβCD | 100 |
| Ethanol | 125.00 |
| EDTA | 4.26 |
| Diethanolamine | pH 5 |
| Water for Injection | q.s. to 1 ml |
| Fill volume | 15 mL |

Manufacturing Procedure:
1. Specified quantity of water for Injection was taken in a suitable container and specified quantity of HPβCD was added under stirring until it formed a clear solution.
2. Specified quantity of polysorbate 80 was added to step 1 solution under continuous stirring.
3. Specified quantity of L-aspartic acid, tartaric acid & citric acid anhydrous were added to step 2 solution under stirring until a clear solution was obtained.
4. Specified quantity of ethanol was added to step 3 solution.
5. Specified quantity of EDTA was added to step 4 solution.
6. Specified quantity of netupitant was added to step 5 solution under stirring until it formed a clear solution.
7. Specified quantity of palonosetron HCl was added to step 6 solution under stirring until it formed a clear solution.
8. The pH of the above solution of step 7 was adjusted to 5.0 by using diethanolamine.
9. Final volume of step 8 solution was made up to 1 ml by using water for Injection.

Samples of the composition Y so obtained were stored and tested to obtain the following results:

TABLE 21

| | | 25° C./60% RH | | 40° C./75% RH | |
|---|---|---|---|---|---|
| Parameters | Initial | 20 Days | 2 Months | 20 Days | 2 Months |
| Description | Clear, Pale yellow color solution, free from visible particles | | | | |
| pH | 4.8 | 4.71 | 4.81 | 4.73 | 4.81 |
| Osmolality (mOsm/Kg) | 299 | 329 | 302 | 318 | 310 |
| Related Substances of Netupitant | | | | | |
| N-oxide Impurity | 0.16 | 0.125 | 0.344 | 0.342 | 0.65 |
| Total Impurities | 0.28 | 0.28 | 0.46 | 0.72 | 0.78 |

Experiment 12

TABLE 22

| Ingredients | Composition Z mg/mL |
|---|---|
| Netupitant | 15.20 |
| Palonosetron HCl | 0.022 |
| Ethanol | 230.7 |
| Polysorbate 80 | 192.3 |
| Citric acid | 12.00 |
| Tartaric acid | 4.00 |
| Aspartic acid | 0.3 |

TABLE 22-continued

| Ingredients | Composition Z mg/mL |
|---|---|
| Propylene glycol | 76.92 |
| Diethanolamine | pH 5 |
| Water for Injection | q.s. to 1 ml |
| Fill volume | 13 mL |

Manufacturing Procedure:
1. Specified quantity of ethanol was taken in a suitable container and specified quantity of netupitant was added under stirring until it formed a clear solution.
2. Specified quantity of polysorbate 80 was added to step 1 solution under continuous stirring.
3. Specified quantity of propylene glycol was added to step 2 solution under continuous stirring.
4. Specified quantity of aspartic acid, tartaric acid & citric acid anhydrous were added to step 3 solution under stirring until a clear solution was formed.
5. Specified quantity of palonosetron HCl was added to step 4 solution under stirring until it formed a clear solution.
6. The pH of the above solution of step 5 was adjusted to 5.0 by using diethanolamine.
7. Final volume of step 6 solution was made up to 1 ml by using water for injection.

Samples of the composition Z so obtained were stored and tested to obtain the following results:

TABLE 23

| Test | Initial | 25° C./60% RH 1 M | 25° C./60% RH 2 M | 40° C./75% RH 1 M | 40° C./75% RH 2 M |
|---|---|---|---|---|---|
| Description | | Clear solution | | | |
| pH | 5.04 | 5.05 | 5.03 | 5.06 | 5.07 |
| Osmolality (mOsm/Kg) | 618 | 627 | 654 | 643 | 643 |
| Assay of Netupitant | 99.10 | 99.90 | 99.90 | 97.90 | 99.2 |
| Assay of Palonosetron HCL | 104.60 | 102.80 | 102.40 | 102.10 | 102.30 |
| Related Substances of Netupitant | | | | | |
| N-oxide Impurity | 0.04 | 0.19 | 0.19 | 0.38 | 0.46 |
| Total Impurities | 0.11 | 0.29 | 0.32 | 0.5 | 0.60 |
| Related Substances of Palonosetron Hydrochloride | | | | | |
| Impurity E | 0.02 | 0.03 | 0.04 | 0.0 | 0.02 |
| Unknown Impurities | 0.16 | 0.21 | 0.09 | 0.06 | 0.03 |
| Total Impurities | 0.18 | 0.24 | 0.13 | 0.09 | 0.05 |

Experiment 13

TABLE 24

| Ingredients | Composition AA mg/mL | Composition AB mg/mL | Composition AC mg/mL |
|---|---|---|---|
| Netupitant | 3.95 | 1.975 | 1.975 |
| Palonosetron HCL | 0.0056 | 0.0028 | 0.0028 |
| Polysorbate 80 | 50.00 | 25.00 | 25.00 |
| Tartaric acid | 0.40 | 0.20 | 0.20 |
| Citric acid | 5.00 | 3.00 | 3.00 |
| HPβCD | 40.00 | 20.00 | 20.00 |
| Ethanol | 40.00 | 20.00 | 20.00 |
| Sodium ascorbate | — | — | 3.00 |
| Sodium formaldehyde sulfoxylate | — | 0.1 | — |
| Sodium Thiosulfate | 0.36 | — | — |
| Monothioglycerol | 0.5 | 0.25 | 0.25 |
| Water for Injection | q.s. to 1 ml | q.s. to 1 ml | q.s. to 1 ml |

Manufacturing procedure:
1. Required quantity of water for injection was taken in a suitable container and specified quantity of HPβCD was added under stirring until it formed a clear solution.
2. Specified quantity of polysorbate 80 was added to step 1 solution with continuous stirring.
3. Specified quantity of ethanol was added to step 2 solution under stirring until it formed a clear solution.
4. Specified quantity of tartaric acid & citric acid anhydrous were added to step 3 solution under stirring until a clear solution was formed.
5. Specified quantity of netupitant was added to step 4 solution with continuous stirring until a clear solution was obtained.
6. Specified quantity of sodium formaldehyde sulfoxylate/ascorbic acid/sodium thiosulfate and monothioglycerol were added to step 5 solution under stirring until a clear solution was formed.
7. Specified quantity of palonosetron hydrochloride was added to step 6 solution under stirring until it formed a clear solution.
8. Final volume of step 8 solution was made up to 1 ml by using purified water.

Samples of the compositions AA, AB and AC so obtained were stored and tested to obtain the following results:

TABLE 25

| Parameters | Composition AA Initial | Composition AA 60° C. 1 W | Composition AC Initial | Composition AC 60° C. 1 W |
|---|---|---|---|---|
| Description | Clear | Clear | Clear | Clear |
| pH | 2.90 | 2.91 | 4.01 | 4 |
| Osmolality (mOsmol/kg) | 983 | 969 | 500 | 496 |
| Netupitant Assay % | 98.1 | 99.7 | 96.4 | 96.2 |
| Palonosetron Hydrochloride | 108.6 | 107.8 | NP | NP |
| Related Substances of Netupitant | | | | |
| N-oxide Impurity | 0.097 | 0.09 | 0.09 | 0.09 |
| Total Impurities | 0.123 | 0.152 | 0.120 | 0.09 |
| Related Substances of Palonosetron Hydrochloride | | | | |
| Impurity E | 0.064 | ND | 0.047 | ND |
| Impurity D | ND | ND | 0.027 | ND |
| Unknown Impurities | 1.763 | 0.371 | 1.34 | 1.05 |
| Total Impurities | 1.83 | 0.37 | 1.45 | 1.14 |

*ND: Not detected; NP: Not performed

TABLE 26

| Parameters | Composition AB | | |
|---|---|---|---|
| | Initial | 60° C. 1 W | 60° C. 2 W |
| Description | Clear | Clear | Clear |
| pH | 2.68 | 2.76 | 2.77 |
| Osmolality (mOsmol/kg) | 423 | 423 | 427 |
| Related Substances of Netupitant | | | |
| N-oxide Impurity | 0.083 | 0.138 | 0.095 |
| Total Impurities | 0.148 | 0.460 | 0.095 |
| Related Substances of Palonosetron Hydrochloride | | | |
| Impurity E | ND | ND | ND |
| Impurity D | ND | ND | ND |
| Unknown Impurities | 1.89 | 1.096 | 1.43 |
| Total Impurities | 1.89 | 1.46 | 1.860 |

*ND: Not detected

Experiment 14

TABLE 27

| Ingredients | Composition AD mg/mL |
|---|---|
| Netupitant | 1.00 |
| Palonosetron HCL | 0.0014 |
| Polysorbate 80 | 12.50 |
| Tartaric acid | 0.4 |
| L-Aspartic acid | 0.03 |
| Citric acid anhydrous | 1.25 |
| HPβCD | 10.00 |
| Ethanol | 10.00 |
| EDTA | 0.32 |
| Diethanolamine | pH adjustment to 5 |
| Water for Injection | q.s. to 1 ml |

Manufacturing Procedure:

1. Required quantity of water for injection was taken in a suitable container and specified quantity of HPβCD was added under stirring until it formed a clear solution.
2. Specified quantity of Polysorbate 80 was added to step 1 solution with continuous stirring.
3. Specified quantity of L-aspartic acid, tartaric acid & citric acid anhydrous were added to step 2 solution under stirring until a clear solution was formed.
4. Specified quantity of ethanol was added to step 3 solution under stirring until it formed a clear solution.
5. Specified quantity of EDTA was added to step 4 solution under stirring until it formed a clear solution.
6. Specified quantity of netupitant was added to step 5 solution with continuous stirring until clear solution was obtained.
7. Specified quantity of palonosetron hydrochloride was added to step 6 solution under stirring until it formed a clear solution.
8. Final solution pH was adjusted to 5 with diethanolamine.
9. The final volume of step 8 solution was made up to 1 ml by using purified water.

Samples of the composition AD so obtained were stored and tested to obtain the following results:

TABLE 28

| Parameters | Composition AD | | |
|---|---|---|---|
| | Initial | 60° C. 1 W | 60° C. 2 W |
| Description | Clear solution | | |
| Osmolality (mOsmol/kg) | 423 | 423 | 427 |
| Related Substances of Netupitant | | | |
| N-oxide Impurity | 0.083 | 0.138 | 0.095 |
| Total Impurities % | 0.148 | 0.460 | 0.095 |
| Related Substances of Palonosetron Hydrochloride | | | |
| Impurity E | ND | ND | ND |
| Impurity D | ND | ND | ND |
| Unknown impurities | 1.89 | 1.096 | 1.43 |
| Total Impurities | 1.89 | 1.46 | 1.860 |

Example 15

TABLE 29

| Ingredients | Composition AE mg/mL | Composition AF mg/mL | Composition AG mg/mL |
|---|---|---|---|
| Netupitant | 3.95 | 3.95 | 1.975 |
| Palonosetron HCL | 0.0056 | 0.0056 | 0.0028 |
| Polysorbate 80 | 50.00 | 50.00 | 25.00 |
| Tartaric acid | 0.40 | 0.40 | 0.20 |
| Citric acid anhydrous | 5.00 | 5.00 | 3.00 |
| HPβCD | 40.00 | 40.00 | 20.00 |
| Ethanol | 40.00 | 40.00 | 20.00 |
| Ascorbic acid | 1.25 | — | — |
| Sodium formaldehyde sulfoxylate | — | 0.2 | — |
| Sodium Thiosuifate | — | — | 0.18 |
| Monothioglycerol | 0.5 | 0.5 | 0.25 |
| Water for injection | Q.S. to 1 ml | Q.S. to 1 ml | Q.S. to 1 mi |
| pH | 2.8 | 2.8 | 2.8 |

Manufacturing Procedure:

1. Required quantity of water for injection was taken in a suitable container and specified quantity of HPβCD was added under stirring until it formed a clear solution.
2. Specified quantity of polysorbate 80 was added to step 1 solution with continuous stirring.
3. Specified quantity of ethanol was added to step 2 solution under stirring until it formed a clear solution.
4. Specified quantity of tartaric acid & citric acid anhydrous were added to step 3 solution under stirring until a clear solution was formed.
5. Specified quantity of netupitant was added to step 4 solution with continuous stirring until a clear solution was obtained.
6. Specified quantity of sodium formaldehyde sulfoxylate/ ascorbic acid/sodium thiosulfate and monothioglycerol were added to step 5 solution under stirring until a clear solution was formed.
7. Specified quantity of palonosetron hydrochloride was added to step 6 solution under stirring until it formed a clear solution.
8. Final volume of step 8 solution was made up to 1 ml by using purified water.
9. pH of the obtained solution was measured and recorded in Table 29.

Having now fully described this invention, it will be understood by those of ordinary skill in the art that it can be performed within a wide equivalent range of parameters without affecting the scope of the invention or any embodiment thereof. All publications, patent applications and patents disclosed herein are incorporated by reference in their entirety.

The invention claimed is:

1. A liquid pharmaceutical composition comprising:
   (a) netupitant;
   (b) at least one pharmaceutically acceptable stabilizer at a concentration of about 1.68 mg/mL to about 21.3 mg/mL selected from the group consisting of tromethamine, phosphoric acid, aspartic acid, tartaric acid, citric acid, maleic acid, ascorbic acid or mixtures thereof;
   (c) at least one pharmaceutically acceptable solubilizer at a concentration of about 0.1 mg/mL to about 200 mg/mL selected from the group consisting of cyclodextrin, cyclodextrin derivatives, polysorbates, propylene glycol and mixtures thereof; and
   (d) at least one pharmaceutically acceptable vehicle,
   wherein netupitant is present at a concentration of about 0.5 mg/mL to about 20 mg/mL,
   wherein the composition is in the form of a solution and has a pH of 2 to 6, and
   wherein the solution is stable and suitable for parenteral administration.

2. The solution according to claim 1, wherein the solution has an osmolality value of about 100 mOsm to about 500 mOsm.

3. The solution according to claim 1, wherein the composition further comprises an antioxidant selected from the group consisting of butylated hydroxytoluene, monothioglycerol, sodium thiosulfate, sodium formaldehyde sulfoxylate and mixtures thereof.

4. The solution according to claim 1, wherein the vehicle is selected from ethanol, water for injection or mixtures thereof.

5. The solution according to claim 1, wherein the solution has netupitant N-oxide content of less than about 0.5% w/w with respect to total amount of netupitant in the solution after storage for 2 months at 25° C. and 60% relative humidity.

6. The solution according to claim 1, wherein the solution is ready-to-use.

7. The solution according to claim 1, wherein the solution is ready-to-dilute.

8. The solution according to claim 1, wherein the solubilizer is present at a concentration ranging from about 0.5 mg/mL to about 100 mg/mL.

9. The solution according to claim 1, wherein netupitant is present at a concentration of about 1.975 mg/mL.

10. A method of preventing acute and/or delayed nausea and/or vomiting associated with initial and/or repeat courses of cancer chemotherapy in a subject in need thereof comprising parenteral administration of the composition of claim 1.

11. A liquid pharmaceutical composition comprising:
    (a) active ingredients netupitant and palonosetron;
    (b) at least one pharmaceutically acceptable stabilizer at a concentration of about 1.68 mg/mL to about 21.3 mg/mL selected from the group consisting of tromethamine, phosphoric acid, aspartic acid, tartaric acid, citric acid, maleic acid, ascorbic acid or mixtures thereof;
    (c) at least one pharmaceutically acceptable solubilizer at a concentration of about 0.1 mg/mL to about 200 mg/mL selected from the group consisting of cyclodextrin, cyclodextrin derivatives, polysorbates, propylene glycol and mixtures thereof; and
    (d) at least one pharmaceutically acceptable vehicle,
    wherein netupitant is present at a concentration of about 0.5 mg/mL to about 20 mg/mL,
    wherein palonosetron is present at a concentration at about 0.001 mg/mL or more;
    wherein the composition is in the form of a solution and has a pH of 2 to 6, and
    wherein the solution is stable and suitable for parenteral administration.

12. A method of preventing acute and/or delayed nausea and/or vomiting associated with initial and/or repeat courses of cancer chemotherapy in a subject in need thereof comprising parenteral administration of the composition of claim 11.

13. The solution according to claim 11, wherein the palonosetron is palonosetron hydrochloride.

14. The solution according to claim 11, wherein palonosetron is present at a concentration of about 0.001 mg/ml to about 0.1 mg/mL.

15. The solution according to claim 11, wherein the solution is physically stable and does not precipitate upon storage for at least 2 months at 25° C. and 60% relative humidity.

16. The solution according to claim 15, wherein the solution is physically stable and does not precipitate upon storage for at least 2 months at 40° C. and 75% relative humidity.

17. The solution according to claim 11, wherein the solution is suitable for intravenous bolus or infusion administration.

18. The solution according to claim 11, wherein the composition further comprises an antioxidant selected from the group consisting of butylated hydroxytoluene, monothioglycerol, sodium thiosulfate, sodium formaldehyde sulfoxylate and mixtures thereof.

19. The solution according to claim 11, wherein the vehicle is selected from ethanol, water for injection or mixtures thereof.

20. The solution according to claim 11, wherein the solution has netupitant N-oxide content of less than about 0.5% w/w with respect to total amount of netupitant in the solution after storage for 2 months at 25° C. and 60% relative humidity.

21. The solution according to claim 11, wherein the solution is ready-to-use or ready-to-dilute.

22. The solution according to claim 11, wherein the solubilizer is present at a concentration ranging from about 0.5 mg/mL to about 100 mg/mL.

23. The solution according to claim 11, wherein the solution is contained in a unit dosage form and comprises a total of 197.5 mg of netupitant and 0.28 mg of palonosetron hydrochloride, palonosetron being present as palonosetron hydrochloride in the unit dosage form.

24. The solution according to claim 11, wherein netupitant is present at a concentration of about 1.975 mg/mL and palonosetron is present as palonosetron hydrochloride at a concentration of about 0.0028 mg/mL.

* * * * *